United States Patent [19]

Johnson

[11] Patent Number: 4,808,180
[45] Date of Patent: Feb. 28, 1989

[54] PROSTHETIC HEART VALVE

[75] Inventor: Keith M. Johnson, Coon Rapids, Minn.

[73] Assignee: Medtronic, Inc., Minneapolis, Minn.

[21] Appl. No.: 44,073

[22] Filed: Apr. 29, 1987

[51] Int. Cl.⁴ .............................................. A61F 2/24
[52] U.S. Cl. ........................................................ 623/2
[58] Field of Search ............................................ 623/2

[56] References Cited

U.S. PATENT DOCUMENTS

| Re. 31,040 | 9/1982 | Possis | 3/1.5 |
|---|---|---|---|
| 3,445,863 | 5/1969 | Wada | 3/1 |
| 3,824,629 | 7/1974 | Shiley | 3/1 |
| 3,835,475 | 9/1974 | Child | 3/1 |
| 4,197,593 | 4/1980 | Kaster et al. | 3/1.5 |
| 4,274,437 | 6/1981 | Watts | 137/527 |
| 4,276,658 | 7/1981 | Hanson et al. | 3/1.5 |
| 4,363,142 | 12/1982 | Meyer | 3/1.5 |
| 4,373,216 | 2/1983 | Klawitter | 3/1.5 |
| 4,443,894 | 4/1984 | Klawitter | 3/1.5 |
| 4,488,318 | 12/1984 | Kaster | 3/1.5 |
| 4,676,789 | 6/1987 | Sorensen et al. | 623/2 |

Primary Examiner—Richard J. Apley
Assistant Examiner—Alan W. Cannon
Attorney, Agent, or Firm—Reed A. Duthler; Joseph F. Breimayer; John L. Rooney

[57] ABSTRACT

An improved heart valve having an annular valve housing and two leaflets supported for pivotable movement within the annular valve housing. Each leaflet is pivoted about an axis displaced from the center of the valve housing. When open, the leaflets pivot away from the center of the valve housing allowing for central flow. The valve leaflets are provided with curved indentations with engage curved projections from the valve housing which serve both to retain the valve leaflets within the housing and to define and control their pivotal movement during opening and closing.

12 Claims, 4 Drawing Sheets

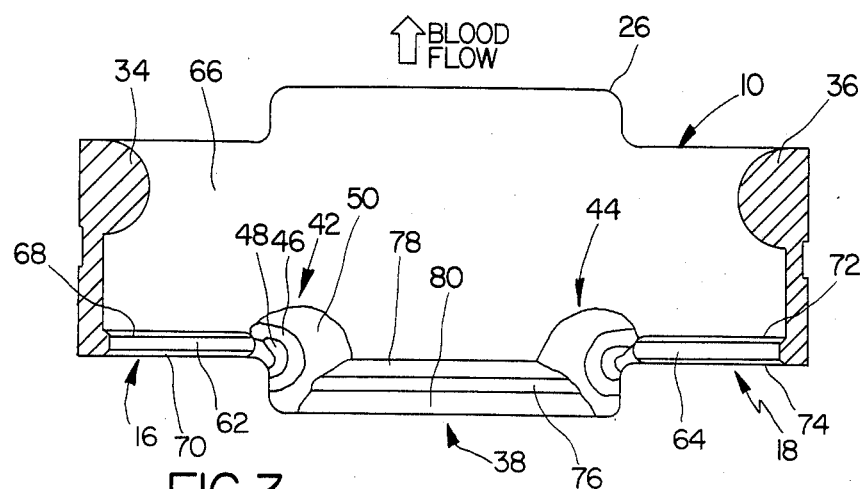
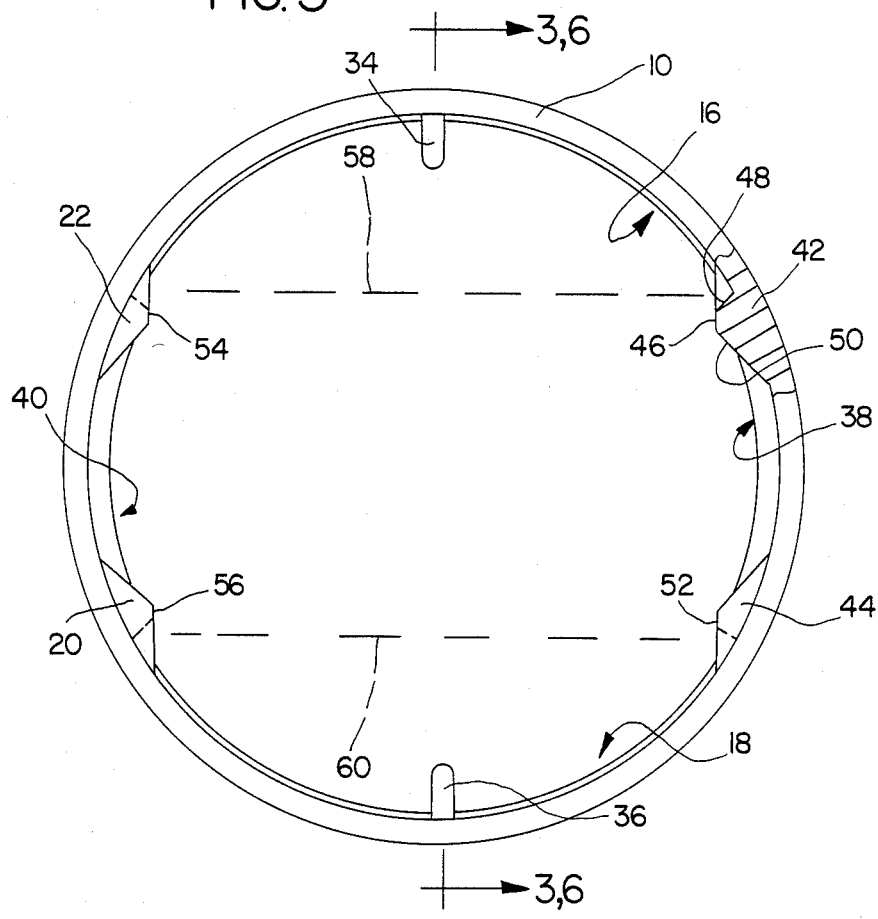

PROSTHETIC HEART VALVE

BACKGROUND OF THE INVENTION

The present invention relates generally to check valves, and particularly to mechanical prosthetic heart valves for human implantation.

Various prosthetic heart valves have been developed to replace diseased or defective human heart valves. These designs have included single leaflet valves such as that disclosed in U.S. Pat. No. 3,445,863 issued to Wada, U.S. Pat. No. 3,835,475 issued to Child, and U.S. Pat. No. 3,824,629 issued to Shiley.

Alternative designs employ two generally flat, semicircular leaflets mounted within a circular valve housing. Some such designs as disclosed in U.S. Pat. No. 4,373,216 issued to Klawitter and U.S. Pat. No. 4,276,658 issued to Hansen employ generally flat leaflets having pivot axes close to the center line of the valve and leaflets which move toward the center of the valve during opening. Other such designs have employed leaflets having pivot axes substantially displaced from the center of the valve which open away from the center of the valve and allow for more centralized blood flow. Such a design is illustrated in U.S. Pat. Re. 31,040 issued to Possis.

A third group of designs employs leaflets having conical or cylindrical surfaces, pivot axes adjacent to or somewhat displaced from the center of the valve and leaflets which open away from the center of the valve to provide for central blood flow. Such designs are disclosed in U.S. Pat. Nos. 4,363,142 issued to Meyer, No. 4,274,437 issued to Watts, and No. 4,488,318 issued to Kaster, and in U.S. Pat. No. 4,476,789 issued to Sorensen and Woien, filed May 16, 1985.

SUMMARY OF THE INVENTION

The present invention, in its preferred embodiment, takes the form of a heart valve having an annular valve housing and two semiconical leaflets pivotally mounted therein. The leaflets pivot about two parallel axes displaced from the center of the valve. When opening, the valve leaflets pivot away from the center of the valve, allowing for centralized blood flow. The leaflets are retained within the valve housing and their pivotal motion is controlled by sets of curved projections on the valve housing and corresponding curved indentations on the valve leaflets. The valve housing cooperates with the leaflets in such a fashion as to minimize chances of impingement or jamming of the valve due to intrusion of material between the valve leaflet and the valve housing.

BRIEF DESCRIPTION OF THE DRAWINGS

FIG. 2 is a top plan view of the valve housing.
FIG. 3 is a sectional view of the valve housing.

DETAILED DESCRIPTION OF THE INVENTION

Figure 1:
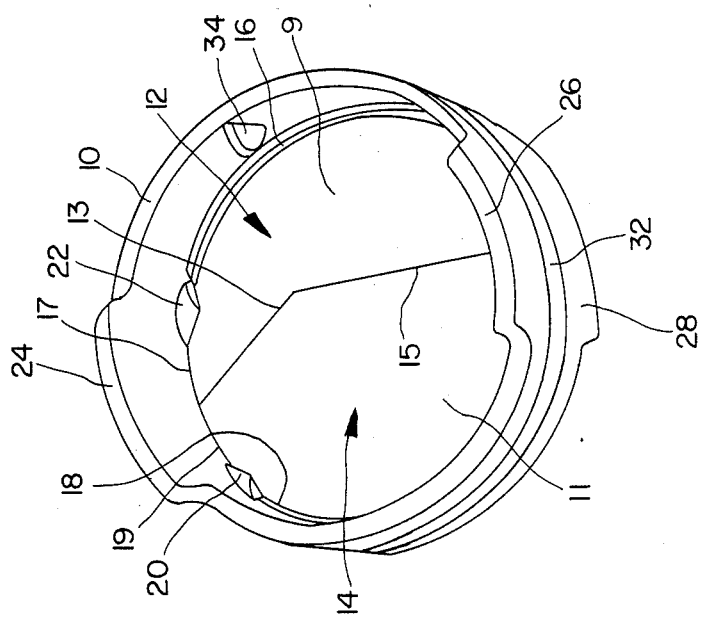
FIG. 1 is a perspective drawing of the downstream side of the valve in the closed position.

FIG. 1 shows a perspective view of the valve from the downstream direction. In this view, the major components of the valve, including the annular housing 10 and the downstream surfaces 9 and 11 of the two leaflets 12 and 14, are visible. Leaflets 12 and 14 each take the general form of one-half of a right conical surface. Leaflets 12 and 14 each have an inner edge, 13 and 15 respectively, and a semicircular outer edge 17 and 19, respectively. In the closed position, as illustrated, inner edges 13 and 15 are adjacent one another, and outer edges 17 and 19 are adjacent housing 10. The preferred materials for construction of the valve are pyrolytic carbon for the housing, as disclosed in U.S. Pat. No. 4,443,894 issued to Klawitter and pyrolytic carbon over a rigid substrate as disclosed in U.S. Pat. Re. 31,040 issued to Possis. Annular housing 10 is provided with ridges 16 and 18 which assist in minimizing back flow between the outer edges 17 and 19 of leaflets 12 and 14, respectively, and housing 10. Also visible are the upper portions of the generally "C" shaped projections 20 and 22. These projections, in conjunction with corresponding projections 42 and 44 (FIG. 2) on the opposite side of housing 10, serve to retain the valve leaflets 12 and 14 within the housing 10 and to define their pivotal motion.

Housing 10 is provided with a circumferential groove 32 in which a metal reinforcing ring may be mounted in order to improve the rigidity of housing 10 and assist in retaining leaflets 12 and 14. As used, housing 10 is preferably rotatably mounted in a suture ring, for example as disclosed in U.S. Pat. No. 4,197,593, incorporated herein by reference in its entirety. When so mounted, projections 24, 26, 28 and a fourth projection corresponding to projection 28 on the upstream side of housing 10 may be engaged to rotate housing 10 from either the upstream or downstream side of the valve. Projection 34 and a corresponding projection 36 (FIG. 2) serve as stops for leaflets 12 and 14, respectively, in their open positions.

FIG. 2 shows a plan view of the valve housing 10 as viewed from the downstream direction. The housing 10 is provided with two ridges 16 and 18, which are adjacent the upper faces 9 and 11 of leaflets 12 and 14 (FIG. 1) along their outer edges 17 and 19, respectively, in their closed positions. The valve housing 10 is also provided with two lower valve seats 38 and 40 which engage the outer edges 17 and 19 of the valve leaflets 12 and 14 (FIG. 1) in their closed positions. In this view, all four "C" shaped projections 20, 22, 42 and 44 are visible. "C" shaped projection 42 is shown in cut away form and is seen to be provided with a generally planar inner surface 46, and with two side surfaces 48 and 50 which slope away from inner surface 46 at a 45° angle. Projections 20, 22, and 44 share this structure. The inner surface 46 of projection 42 is coplanar to the inner surface 52 of projection 44. Similarly, the inner surface 54 of projection 22 is coplanar to the inner surface 56 of projection 20. The planes including inner surfaces 46, 52, 54 and 56 are perpendicular to parallel pivot axes 58 and 60 indicated by dashed lines.

FIG. 3 is a side sectional view of the housing 10. Projections 34 and 36 are both visible in cross section. In this view, it can be seen that ridges 16 and 18 are constructed in a fashion similar to that of the "C" shaped projections 20, 22, 42 and 44 and include inner surfaces 62 and 64 which are parallel to the cylindrical inner surface 66 of housing 10. Ridges 16 and 18 are provided with side surfaces 68, 70, 72 and 74 which slope away from the inner surfaces 62 and 64, respectively, at 45° angles. The same structure is present in lower valve seats 38 and 40 of which only valve seat 38 is visible in this illustration. Valve seat 38 is provided with an inner surface 76, parallel to the cylindrical inner surface 66 of housing 10 and with side surfaces 78 and 80 which slope away from inner surface 76 at a 45° angle.

Figure 5:
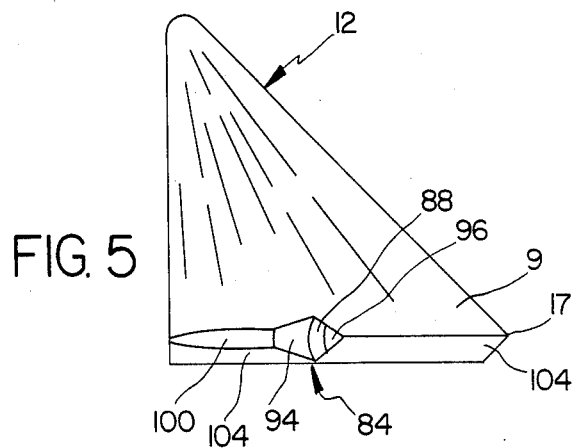
FIG. 5 is a side plan view of one of the leaflets.
Figure 4:
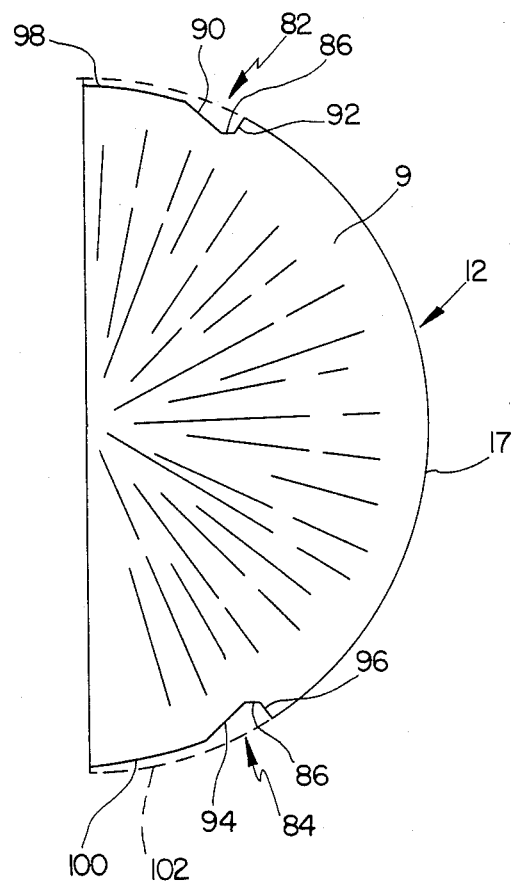
FIG. 4 is a top plan view of one of the leaflets.

The surfaces of "C" shaped projections 20, 22, 42 and 44 are all surfaces of rotation about the pivot axis with which they are associated, and extend over an arc subtending an angle at least as great as the angle through which the leaflets 12 and 14 rotate during opening and closing. In conjunction with corresponding depressions on leaflets 12 and 14, as illustrated in FIGS. 4 and 5 below, they provide a pivot mechanism which allows wiping of surfaces associated with the projections 20, 22, 42 and 44 during pivoting of the leaflets 12 and 14. Because no additional structures are required to retain the leaflets 12 and 14, fabrication of housing 10 is simplified and the housing 10 has fewer structures which impede blood flow.

FIG. 4 shows a top plan view of leaflet 12 of the heart valve of the present invention. Leaflet 12 is seen to be provided with two depressions 82 and 84, each of which has an inner surface 86 and 88, respectively, and side surfaces 90, 92, 94 and 96 which are at 45° angles to the inner surfaces 86 and 88. Depressions 82 and 84 are generally arcuate and have the same radius of curvature as projections 22 and 42, which they engage. Surfaces 88, 94 and 96 correspond to surfaces 46, 48 and 50, respectively, on valve housing 10. Depression 82 corresponds to projection 22 in the same fashion.

In this view, it can be seen that the outer edge 17 of leaflet 12 is semicircular, with the exception of depressions 82 and 84, and with the exception of areas 98 and 100, which are slightly recessed from the semicircle 102 defined by the outer edge 17 of leaflet 12. Recessed areas 98 and 100 allow for clearance between leaflet 12 and housing 10 as the leaflet pivots to the open position. In the open position, with leaflet 12 resting against protrusion 36 (FIG. 2), recessed areas 98 and 100 are slightly spaced from the interior surface 66 (FIG. 2) of housing 10. Alternatively, protrusion 36 (FIG. 2) may be dispensed with, and the opening of leaflet 12 may be limited by recessed areas 98 and 100 resting against the inner wall 66 of housing 10. In this alternative configuration, recessed areas 98 and 100 are preferably configured to lie flat against inner wall 66 of housing 10 when leaflet 12 is in the fully open position.

FIG. 5 is a plan drawing of the side of leaflet 12. In this view, it can be seen that leaflet 12 is provided with a lower surface 104 which extends around the periphery of leaflet 12 at a 90° angle to the upper surface 9 of leaflet 12. In this view, it can be seen that the inner surface 88 of arcuate depression 84 defines an arc having the same radius as the arc defined by inner surface 46 of projection 42 (FIG. 3) with which it cooperates. Similarly, side surfaces 94 and 96 correspond to the side surfaces 50 and 48 of projection 42 (FIG. 2). Recessed area 100 is also visible in this view. It should be noted that lower surface 104 when closed seats against the upper surface 78 of lower valve seat 38 of the housing 10 (FIG. 2).

Depressions 82 and 84 correspond dimensionally to projections 42 and 22 such that when leaflet 12 is inserted in housing 10, leaflet 12 slides freely along projections 42 and 22, but cannot significantly rotate with respect to the particular portion of projections 42 and 22 with which it is engaged. As such, pivotal motion of leaflet 12 is both provided for and constrained by projections 42 and 22 without the necessity for additional projecting pivot structures such as posts, bumps or rods.

Figure 6:
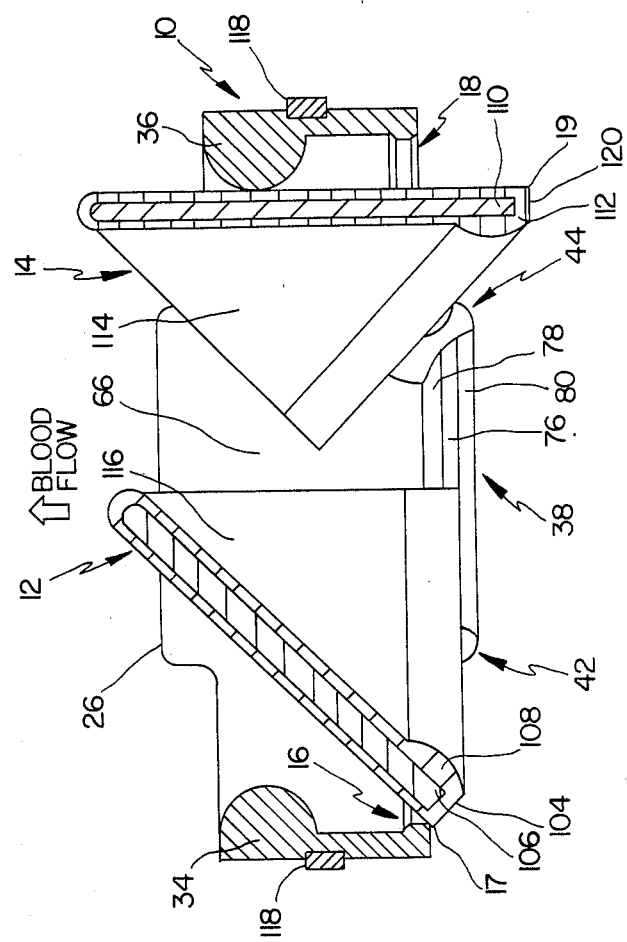
FIG. 6 is a sectional view of the assembled valve.

FIG. 6 is a side sectional view of the assembled valve with leaflet 12 in an open position and leaflet 14 in a closed position. Flow through the valve is predominantly through the center of the valve, although there is limited flow in the areas between the valve leaflets 12 and 14 and the valve housing 10.

In the closed position, leaflets 12 and 14 lie adjacent to one another within housing 10, effectively sealing the valve against reverse flow. When closed, however, the outer edges 17 and 19 and the upper surfaces 9 and 11 of leaflets 12 and 14 are slightly spaced from ridges 16 and 18 to allow for limited back flow through the valve. This is believed beneficial in preventing buildup of thrombotic material on ridges 16 and 18 which are exposed to relatively limited flow of blood while the valve is open. In the closed position, the lower surfaces 120 and 104 of the leaflets 14 and 12 rest on valve seats 38 and 40.

Opening of the valve is accomplished by pressure against the upstream surfaces 116 and 114 of leaflets 12 and 14 which cause the leaflets to rotate away from the center of the orifice of housing 10 by sliding along projections 20, 22, 42 and 44. As flow through the valve decreases, the eddy currents generated by the flow of blood through the valve exert a lateral force on opened leaflets 12 and 14 urging them centrally. As such, the leaflets begin to close promptly upon diminution of forward flow through the valve. After flow through the valve ceases, back pressure against the upper surfaces 9 and 11 of leaflets 12 and 14 finishes the closing action and maintains the leaflets 12 and 14 in a closed position. Because closing of the valve begins prior to cessation of forward flow through the valve, there is minimal back flow through the valve during closing.

The hinging mechanism of this valve is believed to be beneficial to the valve construction in that it is a particularly simple configuration in which hinging and retaining functions are performed by a single projection on each side of the housing engaging with a single depression on each side of the valve leaflet. The "C" shaped projections, 20, 22, 42 and 44 allow for pivoting of the leaflets without translation of the pivot axis while retaining the desired wiping of hinge surfaces during and closing movements. during opening and closing movements.

In addition, the valve as illustrated is particularly easy to construct. The housing is particularly adapted to be fabricated using molding procedures employing a disposable molding mandrel to define the inner surface of the housing 10. The mold recesses corresponding to ridges 16 and 18, "C" shaped projections, 20, 22, 42 and 44, and valve seats 38 and 40 may all conveniently be formed using a single, 45° rotary cutting head. The corresponding recesses on leaflets 12 and 14 are adapted to be cut into the previously formed semiconical leaflets using a similar 45° cutting head. The assembly of the valve is accomplished by slightly deforming the housing 10 of the valve to allow insertion of the "C" shaped projections 20, 22, 42 and 44 into the recesses on the valve leaflets 12 and 14, and thereafter allowing the valve housing 10 to resume its normal configuration. The valve housing 10 may thereafter be made rigid by surrounding it with a ring 118 of titanium, stellite or other implantable metal to prevent deformation of the housing and release of the leaflets.

Although the valve in its preferred form incorporates two semiconical leaflets, it is believed that the novel hinging mechanism disclosed herein would also be applicable to bileaflet valves employing generally flat leaflets as disclosed in U.S. Pat. No. 4,276,658 issued to Hansen et al, generally cylindrical leaflets as disclosed in U.S. Pat. No. 4,274,473 issued to Watts as well as to other single and multiple leaflet configurations.

FIG. 6 illustrates an additional advantage of the valve. Experience has shown that impingement of the valve on a suture or other foreign material lodged between valve leaflets and the valve housing would be likely to occur in the area of ridges 16 and 18. The construction of the valve according to the present invention prevents the leaflets from jamming in the closed position, should such material intrude between the valve seats and the leaflets. During initial opening of the leaflets, the upper surfaces of leaflets 12 and 14 move away from ridges 16 and 18, respectively, along a path nearly perpendicular to surfaces 70 and 74. As such, although material impinging between ridges 16 and 18 and leaflets 12 and 14 may impede complete closure of the valves, it is unlikely that it will impede the opening movement of the valve. This feature is also valuable in leaflets having configurations other than semiconical.

In conjunction with the above descriptions and drawings, I claim:

1. A prosthetic heart valve comprising a housing having a central orifice and an inner wall surrounding said central orifice and a first valve leaflet pivotably mounted to said valve housing along a first pivot axis extending across the orifice of said valve housing, said first leaflet pivoting between a closed position and an open position displaced through a first angle from said closed position;

wherein first and second projections extend from said inner wall of said housing, displaced from said first pivot axis, said first projection extending to and having a first surface substantially tangent to a first plane perpendicular to said first pivot axis, said second projection extending to and having a second surface substantially tangent to a second plane, displaced from said first plane and perpendicular to said first pivot axis, said first and second surfaces of said first and second projections defining first and second arcs, respectively, in said first and second planes, said first and second arcs centered on said first pivot axis, and subtending a second angle at least equal to said first angle; and wherein said first valve leaflet is provided with first and second arcuate depressions, corresponding to and engaging with said first and second projections of said valve housing and defining arcs centered on said first pivot axis.

2. A prosthetic heart valve according to claim 1, therein said first valve leaflet further has an inner edge and an outer edge, said outer edge adjacent said housing when said first leaflet is in its closed position, said inner edge extending across the orifice of said valve housing when said first leaflet is in its closed position, and wherein said valve further comprises a second valve leaflet pivotally mounted to said valve housing along a second pivot axis extending across the orifice of said valve housing, said second leaflet pivoting between a closed position and an open position displaced through a third angle from said closed position, said second leaflet further having an outer edge and an inner edge, said outer edge adjacent said housing when said second leaflet is in its closed position, said inner edge extending across the orifice of said housing when said second leaflet is in its closed position;

wherein third and fourth projections extend from said inner wall of said housing, displaced from said second pivot axis, said third projection extending to and having a third surface substantially tangent to a third plane perpendicular to said second pivot axis, said fourth projection, extending to and having a fourth surface substantially tangent to a fourth plane displaced from said third plane and substantially perpendicular to said second pivot axis, said third and fourth surfaces of said third and fourth projections defining third and fourth arcs, respectively, in said third and fourth planes, said third and fourth arcs centered on said second pivot axis and subtending a fourth angle, greater than or equal to said third angle; and wherein said second valve leaflet is provided with third and fourth arcuate depressions corresponding to and engaging with said third and fourth projections of said valve housing and defining arcs centered on said second pivot axis.

3. A prosthetic valve according to claim 2 wherein said inner edge of said first valve leaflet and said inner edge of said second valve leaflet are adjacent to one another when said first and second leaflets are in said closed position and wherein said inner edges of said first and second valve leaflets are displaced from one another when said first and second leaflets are in said open position.

4. A prosthetic heart valve according to claim 3 wherein said first and second valve leaflets each take the form of one-half of a right conical surface, and wherein said first and second leaflets in their closed position generally take the form of a right conical surface, said inner edges of said first and second leaflets including the apex of said right conical surface.

5. A prosthetic heart valve according to claim 2 or claim 3 or claim 4 wherein said first and second pivot axes are parallel to one another.

6. A prosthetic heart valve according to claim 1 wherein said first valve leaflet has an outer edge, an upper surface and a lower surface, and wherein said first pivot axis is displaced from the center of the orifice of said valve housing in a first direction and wherein said valve housing is further provided with first valve seat means for engaging the lower surface of said first valve leaflet when said first valve leaflet is in its closed position, said valve seat means engaging the lower surface of said first valve leaflet along that portion of the outer edge of said first valve leaflet between said first pivot axis and the center of the orifice of said valve housing.

7. A prosthetic heart valve according to claim 6 wherein said housing further comprises a first ridge extending from said valve housing and located adjacent to said upper surface of said first valve leaflet when said first valve leaflet is in its closed position, said first ridge adjacent to the upper surface of said first valve leaflet along that portion of the outer edge of said first valve leaflet extending in said first direction from said first pivot axis.

8. A prosthetic heart valve according to claim 2 wherein said first valve leaflet has an outer edge, an upper surface, and a lower surface and wherein said first pivot axis is displaced from the center of the orifice of said valve housing in a first direction and said valve housing is provided with first valve seat means for engaging the lower surface of said first valve leaflet when said first valve leaflet is in its closed position, said valve seat means engaging the lower surface of said first valve leaflet along that portion of the outer edge of said first valve leaflet between said pivot axis and the center of the orifice of said valve housing; and wherein said second valve leaflet has an outer edge, an upper surface, and a lower surface and said second pivot axis is displaced from the orifice of said valve housing in said second direction, and wherein said valve housing is provided with second valve seat means for engaging the lower surface of said second valve leaflet when said second valve leaflet is in its closed position, said valve seat means engaging the lower surface of said second valve leaflet along that portion of the outer edge of said second valve leaflet between said second pivot axis and the center of the orifice of said valve housing.

9. A prosthetic heart valve according to claim 8 wherein said housing comprises a first ridge adjacent to said upper surface of said first valve leaflet when said first valve leaflet is in its closed position, said first ridge means adjacent the upper surface of said first valve leaflet along that portion of the outer edge of said first valve leaflet extending from said first pivot axis in said first direction; and wherein said housing comprises a ridge adjacent to the upper surface of said second valve leaflet along in its closed position, said second ridge means adjacent the upper surface of said second valve leaflet along that portion of the outer edge of said second valve leaflet extending from said second pivot axis in said second direction.

10. A prosthetic valve according to claim 5 wherein said first sand third surfaces of said first and third projections are coplanar and wherein said second and fourth surfaces of said second and fourth projections are coplanar.

11. A prosthetic heart valve according to claim 1 wherein said first valve leaflet has an upper surface and a lower surface and wherein said first pivot axis is displaced from the center of the orifice of said valve housing in a first direction and said valve housing is provided with first valve seat means for engaging the lower surface of said first valve leaflet when said first valve leaflet is in its closed position, said valve seat means engaging the lower surface of said first valve leaflet along that portion of said first valve leaflet displaced from said pivot axis in a second direction opposite said first direction.

12. A prosthetic heart valve according to claim 11 wherein said housing comprises a first ridge adjacent to said upper surface of said first valve leaflet when said first valve leaflet is in its closed position, said first ridge means adjacent the upper surface of said first valve leaflet along that portion of the outer edge of said first valve leaflet extending from said first pivot axis in said first direction.

* * * * *